US010537401B2

(12) United States Patent
Dos Santos et al.

(10) Patent No.: US 10,537,401 B2
(45) Date of Patent: Jan. 21, 2020

(54) VITREOUS VISUALIZATION SYSTEM AND METHOD

(71) Applicant: Novartis AG, Basel (CH)

(72) Inventors: Cesario Dos Santos, Newport Beach, CA (US); Andrew David Johnson, Laguna Niguel, CA (US); Ronald Smith, Irvine, CA (US); Gerald David Bacher, Carlsbad, CA (US); Alireza Mirsepassi, Irvine, CA (US); Ryan Takakawa, Aliso Viejo, CA (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 15/793,555

(22) Filed: Oct. 25, 2017

(65) Prior Publication Data
US 2018/0140373 A1 May 24, 2018

Related U.S. Application Data

(60) Provisional application No. 62/424,893, filed on Nov. 21, 2016.

(51) Int. Cl.
*A61B 1/06* (2006.01)
*A61B 90/30* (2016.01)
(Continued)

(52) U.S. Cl.
CPC .............. *A61B 90/30* (2016.02); *A61B 90/20* (2016.02); *A61B 3/0008* (2013.01); *A61B 3/132* (2013.01);
(Continued)

(58) Field of Classification Search
CPC .......... A61B 1/06; A61B 1/313; A61B 3/0008; A61F 2009/00874
See application file for complete search history.

(56) References Cited

U.S. PATENT DOCUMENTS 5,632,740 A * 5/1997 Koch ................... A61B 3/0008
362/554
5,865,829 A 2/1999 Kitajima
(Continued)

FOREIGN PATENT DOCUMENTS

EP 0424686 A1 5/1991
EP 1522290 A1 4/2005
(Continued)

*Primary Examiner* — Jacqueline T Johanas
*Assistant Examiner* — Michelle C Eckman

(57) ABSTRACT

The present disclosure provides a vitreous visualization system including a vitreous illuminator including a vitreous visualization light source and a vitreous visualization tool that transmits lights from the vitreous visualization light source into an eye having vitreous, a pupil, and a vitreous-pupil axis. The vitreous visualization system further includes a general illuminator, which may include a general light source and a general illumination tool that transmits light from the general light source into the eye. The present disclosure further provided a vitreous visualization system including only a vitreous illuminator that transmits light from the vitreous visualization light source into an eye having vitreous, a pupil, a vitreous-pupil axis, and a retina at an angle B with the vitreous-pupil axis of the eye such that the brightness of vitreous in the eye is higher than the brightness of the retina of the eye.

23 Claims, 7 Drawing Sheets

(51) Int. Cl.
  *A61B 90/20* (2016.01)
  *A61B 90/00* (2016.01)
  *A61B 3/00* (2006.01)
  *A61B 3/13* (2006.01)
  *A61F 9/007* (2006.01)

(52) U.S. Cl.
  CPC ......... *A61B 90/37* (2016.02); *A61B 2090/306* (2016.02); *A61B 2090/309* (2016.02); *A61F 9/00736* (2013.01)

(56) References Cited

U.S. PATENT DOCUMENTS

| | | | |
|---|---|---|---|
| 6,540,390 | B2 | 4/2003 | Toth et al. |
| 6,551,291 | B1 * | 4/2003 | de Juan, Jr. ......... A61F 9/00727 604/289 |
| 8,118,790 | B2 | 2/2012 | Dacquay et al. |
| 8,172,834 | B2 | 5/2012 | Bhadri et al. |
| 8,371,695 | B2 | 2/2013 | Papac et al. |
| 9,962,226 | B2 | 5/2018 | Brennan et al. |
| 10,016,248 | B2 | 7/2018 | Mirsepassi et al. |
| 2004/0004846 | A1 | 1/2004 | Steen et al. |
| 2005/0245916 | A1 * | 11/2005 | Connor .................. A61F 9/008 606/4 |
| 2006/0245702 | A1 * | 11/2006 | Cazzini .............. A61B 1/00165 385/115 |
| 2008/0004608 | A1 | 1/2008 | Dacquay et al. |
| 2008/0246920 | A1 | 10/2008 | Buczek et al. |
| 2009/0163897 | A1 | 6/2009 | Skinner |
| 2010/0198200 | A1 | 8/2010 | Horvath |
| 2010/0318074 | A1 * | 12/2010 | Dacquay ................ A61F 9/008 606/4 |
| 2011/0037948 | A1 * | 2/2011 | Horvath ............... A61B 1/0653 351/221 |
| 2011/0105999 | A1 | 5/2011 | Akahoshi |
| 2011/0245820 | A1 * | 10/2011 | Papac .................. A61B 1/0653 606/15 |
| 2012/0041461 | A1 * | 2/2012 | McCollam .......... A61F 9/00736 606/170 |
| 2012/0050684 | A1 * | 3/2012 | Smith .................. A61B 3/0008 351/221 |
| 2012/0051042 | A1 * | 3/2012 | Artsyukhovich ...... A61B 90/30 362/231 |
| 2013/0085326 | A1 * | 4/2013 | Scheller ............. A61M 3/0266 600/106 |
| 2013/0131652 | A1 * | 5/2013 | Dick ...................... A61F 9/008 606/4 |
| 2014/0121469 | A1 * | 5/2014 | Meckel ............... A61F 9/00821 600/249 |
| 2014/0180264 | A1 | 6/2014 | Diao et al. |
| 2016/0113722 | A1 * | 4/2016 | Heeren ............... A61F 9/00763 600/249 |
| 2016/0175149 | A1 * | 6/2016 | McDonell ........... A61F 9/00745 600/249 |
| 2016/0296112 | A1 * | 10/2016 | Fletcher .................... A61B 3/14 |
| 2016/0302878 | A1 | 10/2016 | Kern |
| 2016/0346058 | A1 | 12/2016 | Bacher et al. |
| 2017/0165114 | A1 * | 6/2017 | Hallen .................. A61B 1/313 |
| 2017/0172694 | A1 | 6/2017 | Dos Santos et al. |
| 2017/0172792 | A1 * | 6/2017 | Mirsepassi ............... A61F 9/007 |
| 2017/0252121 | A1 * | 9/2017 | Diao ...................... A61B 90/30 |
| 2017/0290704 | A1 * | 10/2017 | Mercado ........... A61F 9/00736 |
| 2017/0333151 | A1 * | 11/2017 | Maholtra ............... A61B 90/30 |
| 2018/0062344 | A1 * | 3/2018 | Smith .................... H05B 37/02 |
| 2018/0078315 | A1 * | 3/2018 | Ren ....................... A61B 34/20 |
| 2018/0104101 | A1 * | 4/2018 | Lopez ................. A61F 9/00763 |
| 2018/0133057 | A1 * | 5/2018 | Diao .................. A61F 9/00763 |
| 2018/0140179 | A1 * | 5/2018 | LaBelle ............... A61B 3/0008 |
| 2018/0140373 | A1 * | 5/2018 | Dos Santos ........... A61B 90/30 |
| 2018/0147087 | A1 * | 5/2018 | Bacher ................ A61B 3/0008 |
| 2018/0271643 | A1 * | 9/2018 | Gunn ...................... A61F 2/14 |

FOREIGN PATENT DOCUMENTS

| | | | |
|---|---|---|---|
| WO | 9613216 | A1 | 5/1996 |
| WO | 99/48557 | A1 | 9/1999 |
| WO | 0059396 | A1 | 10/2000 |

* cited by examiner

VITREOUS VISUALIZATION SYSTEM AND METHOD

TECHNICAL FIELD

The present disclosure relates to ophthalmic surgery and surgical equipment, and more specifically, to a vitreous visualization system and methods of vitreous visualization during ophthalmic surgery.

BACKGROUND

Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is surgery performed on the eye or any part of the eye. Ophthalmic surgery is regularly performed to repair retinal defects, repair eye muscles, remove cataracts or cancer, or to restore or improve vision. During ophthalmic surgery, it is often useful to visualize the vitreous, either to allow its removal or for other reasons. The vitreous is a gel-like substance located in the eye, behind the lens and in front of the retina, which is portion of the eye that contains photoreceptors sensitive to light. The vitreous is thus very transparent and colorless to allow light to pass largely unimpeded to the retina. The vitreous is mostly composed of water and normally contains no blood vessels, allowing it to be transparent and colorless. Although these properties are excellent for the normal functions of the vitreous, they make it very hard to see during ophthalmic surgery.

SUMMARY

The present disclosure provides a vitreous visualization system including a vitreous illuminator. The vitreous illuminator may include a vitreous visualization light source and a vitreous visualization tool that transmits lights from the vitreous visualization light source into an eye having vitreous, a pupil, and a vitreous-pupil axis. The vitreous visualization system further includes a general illuminator, which may include a general light source and a general illumination tool that transmits light from the general light source into the eye.

The present disclosure also provides another vitreous visualization system including a vitreous illuminator. The vitreous illuminator may include a vitreous visualization light source and a vitreous visualization tool that transmits light from the vitreous visualization light source into an eye having vitreous, a pupil, a vitreous-pupil axis, and a retina at an angle B with the vitreous-pupil axis of the eye such that the brightness of vitreous in the eye is higher than the brightness of the retina of the eye.

Aspects of these two vitreous visualization systems and their methods of use may be combined with one another unless clearly mutually exclusive. In addition, the two vitreous visualization systems and their methods of use may include at least the following additional features, which may also be combined with one another unless clearly mutually exclusive: i) the system may also include a vitreous conduit that transmits light from the vitreous visualization light source to the vitreous visualization tool; ii) the vitreous visualization light source may be located within the vitreous visualization tool; iii) the vitreous visualization light source may generate light at a wavelength corresponding to a visible color and the general light source may generate white light; iv) the vitreous visualization light tool may transmit light into the eye at an angle of illumination A that is less than 45 degrees; v) the vitreous visualization tool may have a numeric aperture of less than 0.30; vi) the general illumination tool may transmit light into the eye at an angle of illumination C, which is less than 75 degrees; vii) the luminous flux of the vitreous illuminator, as measured at the tip of the vitreous visualization tool, may be at least five times higher than the luminous flux of the general illuminator, as measured at the tip of the general illumination tool; viii) the vitreous visualization tool may transmit light into the eye at an angle of illumination A, and an angle B formed between the center of angle of illumination A and the vitreous-pupil axis may be less than 100 degrees; ix) the general illumination tool may transmit light into the eye at an angle of illumination C, and an angle D formed between the center of angle of illumination D and the vitreous-pupil axis may be at least 90 degrees; x) the vitreous illuminator may generate pulses of light; xi) the vitreous visualization tool may have a luminous flux at its tip within the eye of 10 lumens or less; xii) the distance between the vitreous visualization light source and the vitreous may be less than three meters; xiii) the vitreous visualization tool may be combined with a surgical tool; xiv) the vitreous visualization light source and the general light source may be a single combined light source; xv) the vitreous visualization tool and the general illumination tool may form a combined tool; xvi) the combined tool may include at least two optical fibers including at least one that transmits light from the vitreous visualization light source and at least one that transmits light from general light source; xvii) the combined tool may include a multi-core optical fiber having an core optical fiber that transmits light from the vitreous visualization light source and an exterior optical fiber that transmits light from the general light source.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

The present disclosure provides systems and methods for visualizing the vitreous during ophthalmic surgery. In particular, these systems and methods may be used during vitreoretinal surgery and they may be especially useful during a vitrectomy, in which all or a part of the vitreous is removed from the eye. Systems and methods of the present disclosure improve the ability to see the vitreous as compared to current systems and methods by including a vitreous illuminator. Current systems and methods for visualizing the vitreous do not include a specific vitreous illuminator. Instead, they rely on a general illuminator, such as a system including an endoilluminator, that is typically designed to illuminate the retina or other eye structures and not the vitreous. Such general illuminators typically provide a broad angle of illumination, whereas a vitreous illuminator as described herein provides a focused light source, with a low angle of illumination. In addition, a vitreous illuminator as described herein may provide light having other properties that facilitate visualizing the vitreous during ophthalmic surgery, such as a particular color, a lower angle of illumination, or with greater luminous flux than is typically provided by a general illuminator. Overall, the use of a separate vitreous visualization system may allow the normally clear vitreous to have a smoky appearance, similar to normally invisible dust particles in a laser beam or bright, focused flashlight beam.

Figure 1:
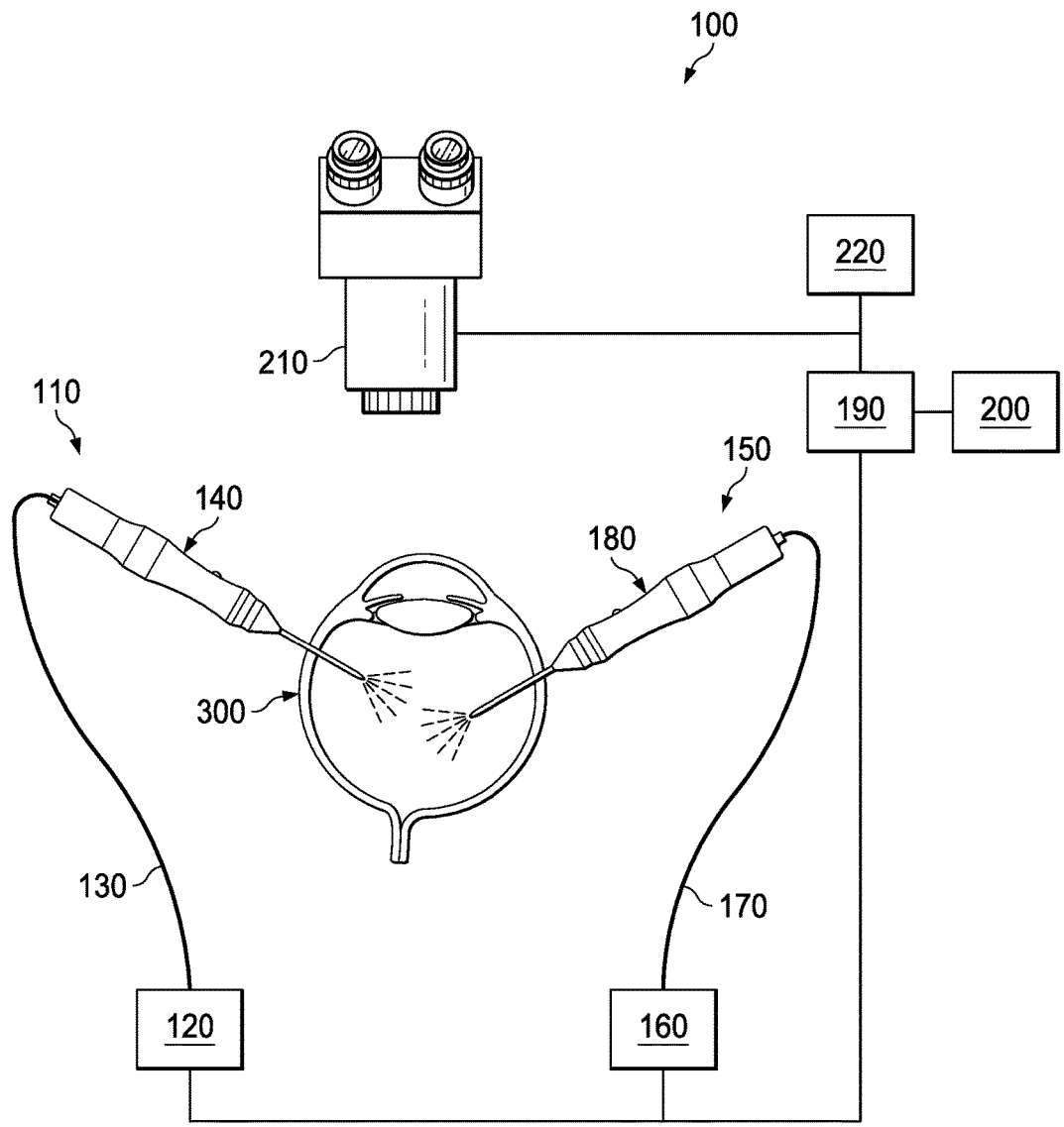
FIG. 1 is a schematic representation of a vitreous visualization system with surgical instruments inserted in an eye to allow visualization of the vitreous during ophthalmic surgery.

Referring now to FIG. 1, vitreous visualization system 100 includes vitreous illuminator 110, which includes vitreous visualization light source 120, vitreous conduit 130, such as an optical fiber, and vitreous visualization tool 140. Vitreous visualization light source 120 generates light, which is transmitted through vitreous conduit 130 to vitreous visualization tool 140, which may be inserted into and transmit the light into eye 300. Vitreous visualization light source 120 may include any of a variety of light sources, but in particular it may include a supercontinuum laser that is able to provide enough light to vitreous conduit 130 to illuminate the vitreous of eye 300. Vitreous visualization light source may include a white light source. If the light is a particular color, such as yellow, blue or green, vitreous visualization light source 120 may include a monochromatic light source, such as a monochromatic laser. If vitreous visualization light source 120 includes a laser, it may be any type of laser suitable to produce the selected type of light. For example, a supercontinuum laser may be used for white light. Yellow, green, and blue lasers may also be used as these colors render the vitreous readily visible against the retina and their respective wavelengths are scattered well by the vitreous, also rendering it more visible. Lasers that produce colors that are more similar to the retina or at wavelengths that are not scattered well by the vitreous, such as red or orange lasers, may still be used, but their use may be limited to particular situations in which the color of light confers a different advantage.

Vitreous conduit 130 may include any material that substantially transmits light, but it particular, it may be an optical fiber, such as a 25 µm core fiber. Typically, if a laser and an optical fiber are used, the optical fiber is not part of the laser, which may incorporate a different fiber, such as a photonic crystal fiber.

Vitreous illuminator 110 may be a particularly designed instrument, but it may also be a repurposed instrument already in existence, such as a laser probe commonly used for coagulation after a vitrectomy has been performed. Such an instrument may be used as a vitreous illuminator 110 by turning down its power.

Figure 7:
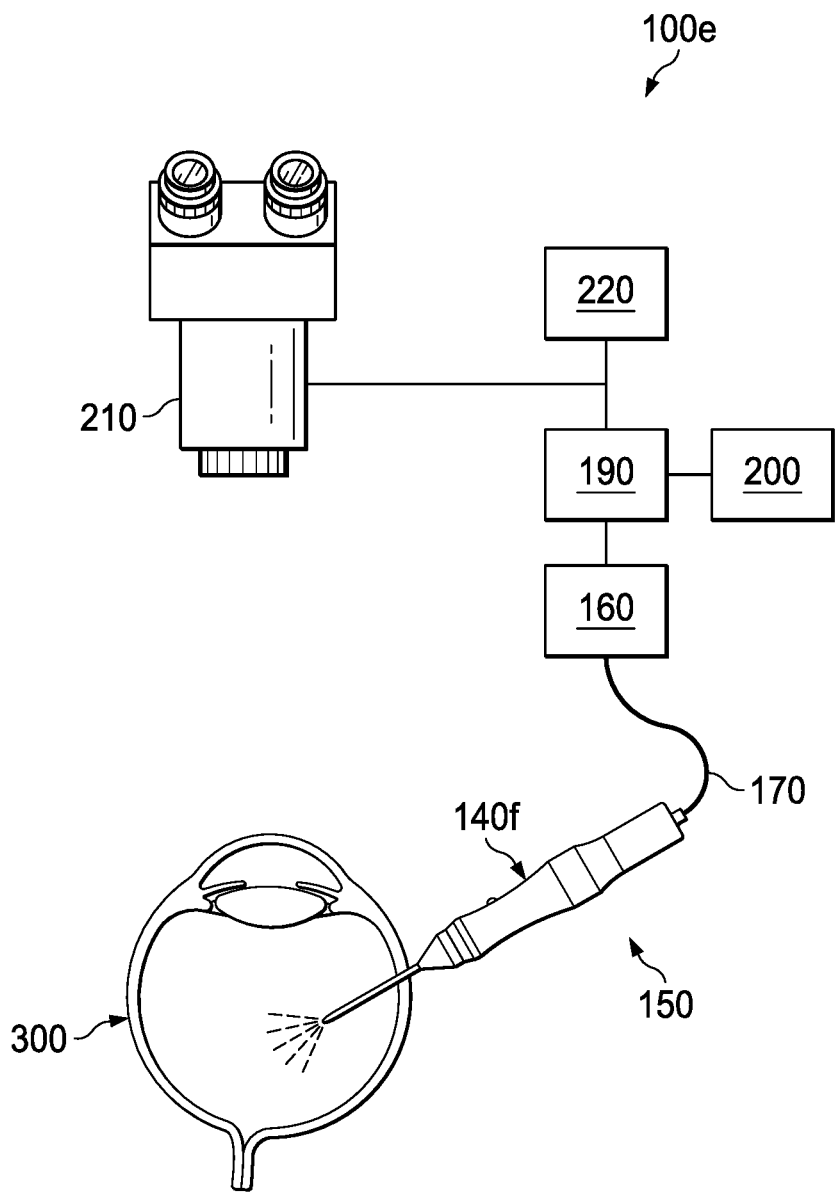
FIG. 7 is a schematic representation of a vitreous visualization system including a combined vitreous visualization and general illumination tool, with surgical instruments inserted in an eye to allow visualization of the vitreous during ophthalmic surgery.
Figure 8:
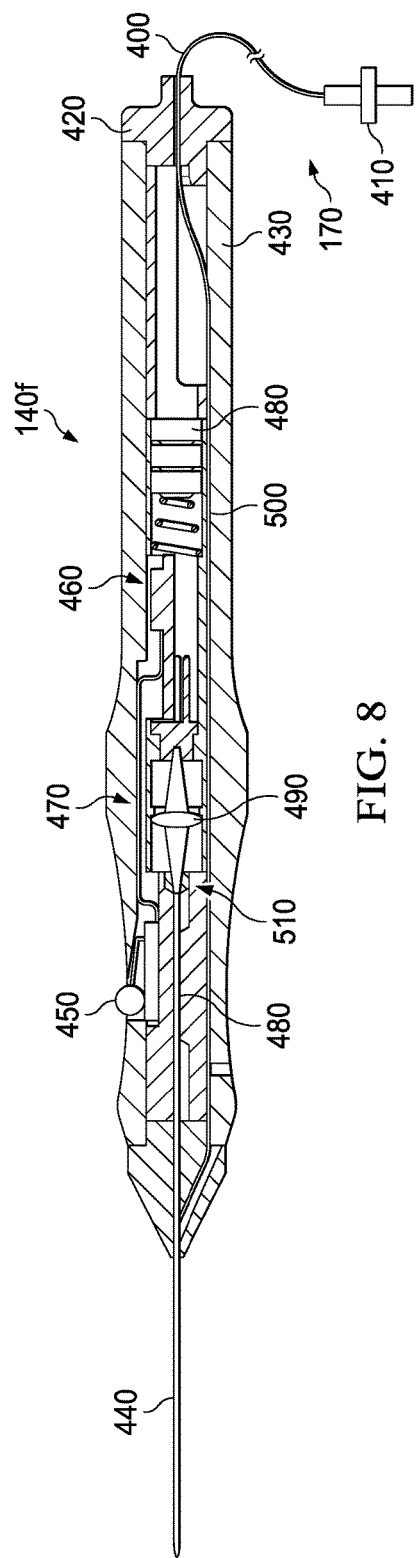
FIG. 8 is a schematic representation of a portion of a vitreous visualization system including a cross-section schematic representation of a combined vitreous visualization tool and general illumination tool.
Figure 9:
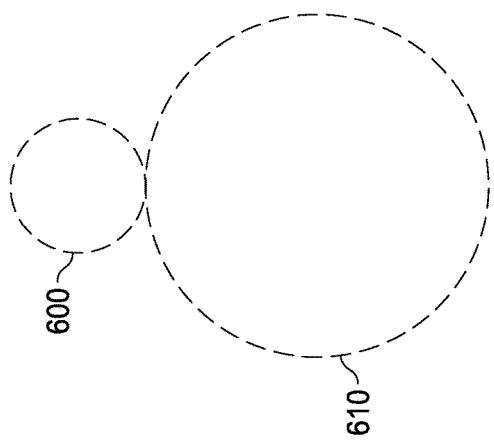
FIG. 9 is a schematic representation of light cones produced by the tool of FIG. 8.

Although vitreous visualization system 100 as illustrated in FIG. 1, has a vitreous visualization light source 120 that is separate from vitreous visualization tool 140, it is also possible for vitreous visualization light source 120 to be located in vitreous visualization tool 140, in which case vitreous conduit 130 may be unnecessary. One such configuration is illustrated in FIGS. 7-9.

Vitreous visualization system 100 may include a number of optional additional components as well, some of which are also illustrated in FIG. 1. For instance, vitreous visualization system 100 may include general illuminator 150, which includes general light source 160, general conduit 170, such as an optical fiber, and general illumination tool 180, such as an endoilluminator. General light source 160 generates light, which is transmitted by general conduit 170 to general illumination tool 180, which may be inserted into and transmit the light into eye 300. General illumination light source 160 may include a laser, a white light source, or any other suitable light source.

Although vitreous visualization system 100 as illustrated in FIG. 1, has a general light source 160 that is separate from general illumination tool 180, it is also possible for general light source 160 to be located in general illumination tool 140, in which case general conduit 170 may be unnecessary.

Vitreous visualization system 100 is depicted in FIG. 1 with separate vitreous visualization and general light sources and separate vitreous and general conduits. However, a combined light source and a partially combined conduit with a splitter may be used instead, particularly if vitreous visualization tool 140 is able to focus the light and provide a narrower angle of illumination than general illumination tool 180, or if vitreous visualization is achieved by a difference in the angles between vitreous visualization tool 140 and general illumination tool 180 and the vitreous-pupil axis of eye 300 (as illustrated in FIGS. 2-5).

The portions of vitreous visualization tool 140 and general illumination tool 180 that actually enter eye 300 may be small to avoid trauma to the eye and to allow their use with existing surgical equipment. For instance, they may be 20 gauge or smaller, 23 gauge or smaller, or 25 gauge or smaller.

Vitreous visualization system 100 may further include a processor 190 that may be in communication with and may control one or both of vitreous illuminator 110 and general illuminator 150. For instance, processor 190 may control whether one or both of vitreous visualization light source 120 or general light source 160 are on or the luminous flux or wavelengths of light one or both provide. Processor 190 may vary the on/off status or luminous flux or wavelengths of light, for example in response to input from controller 200, to improve visibility of the vitreous of eye 300 or to avoid phototoxicity or other negative effects.

Processor 190 may include, for example a microprocessor, microcontroller, digital signal processor (DSP), application specific integrated circuit (ASIC), or any other digital or analog circuitry configured to interpret and/or execute program instructions and/or process data. Processor 190 may interpret and/or execute program instructions and/or process data stored in a memory. The memory may be configured in part or whole as application memory, system memory, or both. The memory may include any system, device, or apparatus configured to hold and/or house one or more memory modules. Each memory module may include any system, device or apparatus configured to retain program instructions and/or data for a period of time (e.g., computer-readable media). The various servers, electronic devices, or other machines described may contain one or more similar such processors or memories for storing and executing program instructions for carrying out the functionality of the associated machine.

Vitreous visualization system 100 may also includes a surgical microscope 210, a display 220, such as a screen or head up display, or both. Surgical microscope 210 may allow the user to view eye 300 directly, or it may display an image of eye 300, such as a digital image generated by processor 190 or another processor. In either case, surgical microscope 210 may display other information in addition to an image of eye 300. Such other information may be generated by processor 190 or another processor and may include graphic or textual information, such as warnings, graphs, color coding, or augmented reality information. Display 220 may similarly display an image of eye 300 generated by processor 190 or another processor and other information generated by processor 190 or another processor. Such information may include graphic or textual information, such as warnings, graphs, color coding or augmented reality information. The information displayed on display 220 may not match that displayed on or seen using surgical microscope 210. Controller 200 may be used to control the information displayed on display 220 and surgical microscope 210.

Although one controller 200 is depicted as working through processor 190, one or more controllers 200 may be directly located in vitreous illuminator 110 or general illuminator 150. For instance, a controller 200 may be integrated into vitreous visualization tool 140 or general illumination tool 180 or a combined tool as described below, where it may control the on/off status, luminous flux, wavelength, or other properties of light for vitreous visualization or general illumination. A controller 200 might also be integrated into vitreous visualization light source 120 or general light source 160. A controller 200, even if not integrated into vitreous illuminator 110 or general illuminator 150, may control one of both of these without the assistance of processor 190.

Processor 190 may also perform other functions relating to other components of the surgery and other instruments, or relating to vitreous visualization system 100. For example, processor 190 may track the total amount of light output by vitreous illuminator 110 or general illuminator 150, or both, and may provide this information to the surgeon or even automatically adjust light output so as to not exceed preset thresholds for total light output during a procedure or part of a procedure or on a portion of the eye.

The brightness of the vitreous of eye 300 depends on at least five factors; i) the luminous flux of vitreous illuminator 110, ii) the relative luminous flux of vitreous illuminator 110 and general illuminator 150, iii) the distance between vitreous visualization source 120 and the vitreous of eye 300, iv) the angle of illumination of vitreous visualization tool 140, and v) the angle formed between the center of the angle of illumination of vitreous visualization tool 140 and the vitreous-pupil axis of eye 300.

The luminous flux of vitreous illuminator 110 is largely determined by the luminous flux of vitreous visualization light source 120, which may be controlled by processor 190 or another processor, optionally with input from controller 200, or directly via a controller, such as controllers 450 and 460 in FIGS. 8 and 9. Luminous flux may be decreased by vitreous conduit 130 and vitreous visualization tool 140, but these components are generally designed to avoid a decrease in luminous flux. The luminous flux of vitreous illuminator 110, as measured at the tip of vitreous visualization tool 140 may be 10 lumens or less. It may also be at least 0.5 lumens, at least 1 lumen, or at least 2 lumens. The luminous flux may also be between 0.5 lumens and 10 lumens, between 1 lumen and 10 lumens, or between 2 lumens and 10 lumens. Light exiting the tip of vitreous illuminator 110 will typically diverge less rapidly than light exiting the tip of general illuminator 150. This leads to increased light intensity (light per unit area).

The visibility of the vitreous is directly related to the ratio of brightness of the vitreous to brightness of retina. If the ratio is higher, the vitreous is more visible. In systems with both a vitreous illuminator 110 and a general illuminator 150, the relative luminous flux of these components largely determines the ratio of brightness of the vitreous to brightness of the retina. The relative luminous flux of vitreous illuminator 110 as compared to general illuminator 150 is largely determined by the relative luminous flux of vitreous visualization light source 120 and general light source 160, one or both of which may be controlled by processor 190 or another processor, optionally with input from controller 200, or directly via a controller, such as controllers 450 and 460 in FIGS. 8 and 9. Luminous flux may be decreased by vitreous conduit 130, vitreous visualization tool 140, general conduit 170, and general illumination tool 180, but these components are generally designed to avoid a decrease in luminous flux.

The luminous flux of vitreous illuminator 110, as measured at the tip of vitreous visualization tool 140, may be at least 5 times higher, at least 10 times higher, or at least 20 times higher than the luminous flux of general illuminator 150, as measured at the tip of general illumination tool 180. For a combined tool, the flux from vitreous illuminator components and general illuminator components may be measured at the tip of the combined tool and compared. Regardless of whether separate or combined tools are used, the general illuminator components may have a larger tip diameter, typically a fiber diameter, than the vitreous visualization components and the general illumination light may have a higher divergence than the vitreous visualization light. The ratio of the areas illuminated by the general illumination light as compared to the vitreous visualization light will increase as distance from the tool tips increases. These differences in area affect the light intensity at any region in the eye, which may be calculated or estimated in order to ensure that vitreous visualization is actually improved and to avoid phototoxicity damage.

In systems with only a vitreous illuminator 110 and no general illuminator 150, the ratio of brightness of the vitreous to brightness of the retina may be determined by ambient light entering the eye as well as the amount of light that reaches the retina from vitreous illuminator 110, which may be affected by a number of factors including the luminous flux of vitreous illuminator 110, its angle of illumination, and its position within eye 300.

The distance between vitreous visualization light source 120 and the vitreous of eye 300 is determined largely by the length of vitreous conduit 130. Lower distances result in better visualization, so the length of vitreous conduit 130 may be the shortest distance acceptable to allow the ophthalmic surgery to be safely performed, given the configuration of other equipment and surgeon preferences and parameters. Vitreous conduit 130 may be provided in different lengths. Information regarding the length of vitreous conduit 130 may be provided to processor 190 or another processor controlling vitreous visualization light source 120 so that appropriate adjustments may be made. In general vitreous conduit 130 may be less than three meters in length, two meters in length, or one and a half meters in length, or between any of these endpoints.

Vitreous conduit 130 may be absent entirely in some vitreous visualization systems, such as that described in FIG. 7-9. In such systems, where vitreous visualization light source 120 is located within vitreous visualization tool 130, the distance between vitreous visualization light source 120 and the vitreous of eye 300 is determined largely by the length of vitreous visualization tool 140 and the position of vitreous visualization light source 120 within it.

The angle of illumination of vitreous visualization tool 140, indicted by angle A in FIGS. 2-5, may be less than 45 degrees, less than 35 degrees, less than 30 degrees, less than 25 degrees, or less than 20 degrees. In general, vitreous visualization light source 140 may focus light and achieve a low angle of illumination A by having a numeric aperture of less than 0.30, less than 0.25 less than 0.15, less than 0.12, or less than 0.10 as measured in air. A small numeric aperture may be achieved in a variety of ways. For instance, the end of a optical fiber in vitreous visualization light source 140 may be tapered. This may achieve a small numeric aperture even when using an optical fiber otherwise usable in a general illumination tool. In addition an optical fiber otherwise usable in a general illumination tool, such as one having a numeric aperture of 0.50 to 0.63, may be used to produce a low angle of illumination by illuminating the optical fiber with a light source, such as a laser beam, that has a low numeric aperture, such as less than 0.15, less than 0.14, or less than 0.12. The light source may be focused axially well within the optical fiber and not at the entrance face of the fiber. If the optical fiber has a tapered end proximate the light source, then the light source may be focused past the tapered end within the optical fiber.

The angle between the center of angle of illumination A and the vitreous-pupil axis of eye 300, indicated as angle B in FIGS. 2-5, also affects visibility of the vitreous. The vitreous is also more visible if angel B is lower. If angle B is lower, then light from vitreous visualization tool 140 is directed more towards the exterior of eye 300 and less towards the retina. This helps avoid light from vitreous visualization tool 140 also illuminating the retina and thereby decreasing the ratio of brightness of the vitreous to brightness of the retina. Angle B may be less than 100 degrees, less than 90 degrees, less than 80 degrees, or less than 60 degrees.

Angles B and D as well as the luminous flux of both vitreous illuminator 110 and general illuminator 150 may change during the course of an ophthalmic surgery.

Figure 2:
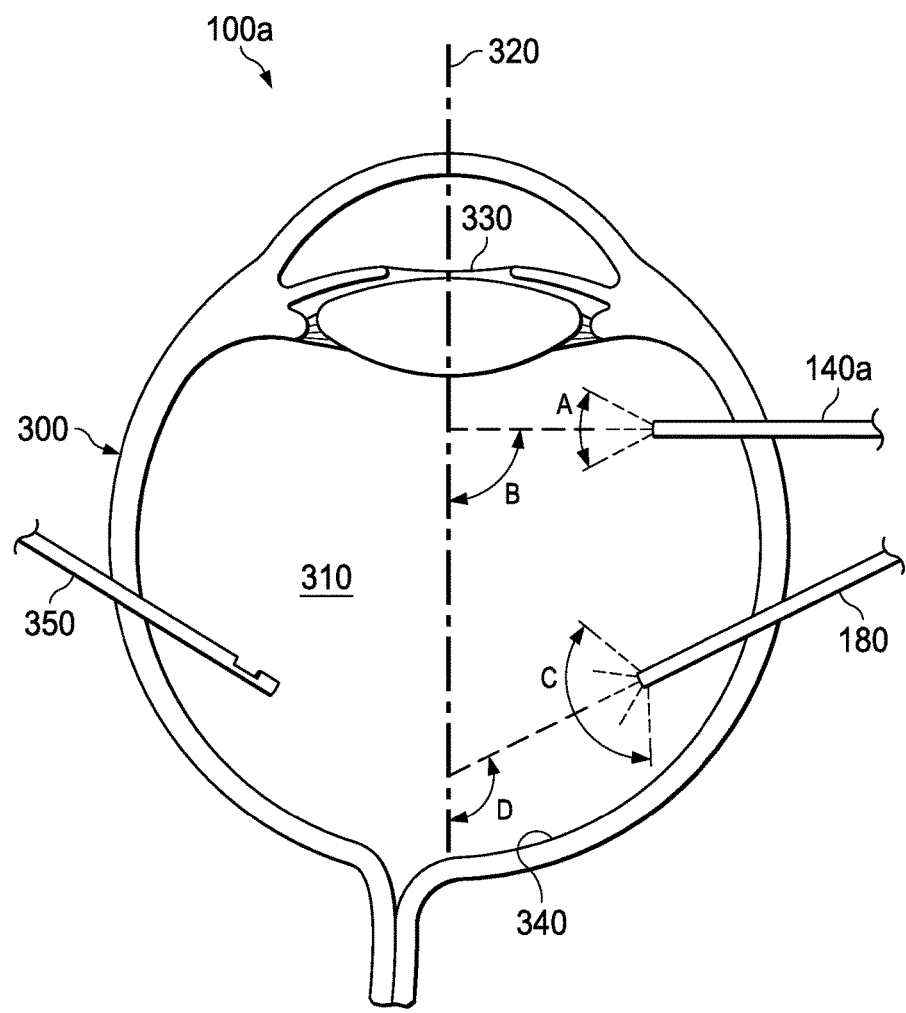
FIG. 2 is a schematic representation of a vitreous visualization system, including a separate vitreous visualization tool and general illumination tool both inserted in an eye to allow visualization of the vitreous during ophthalmic surgery.
Figure 3:
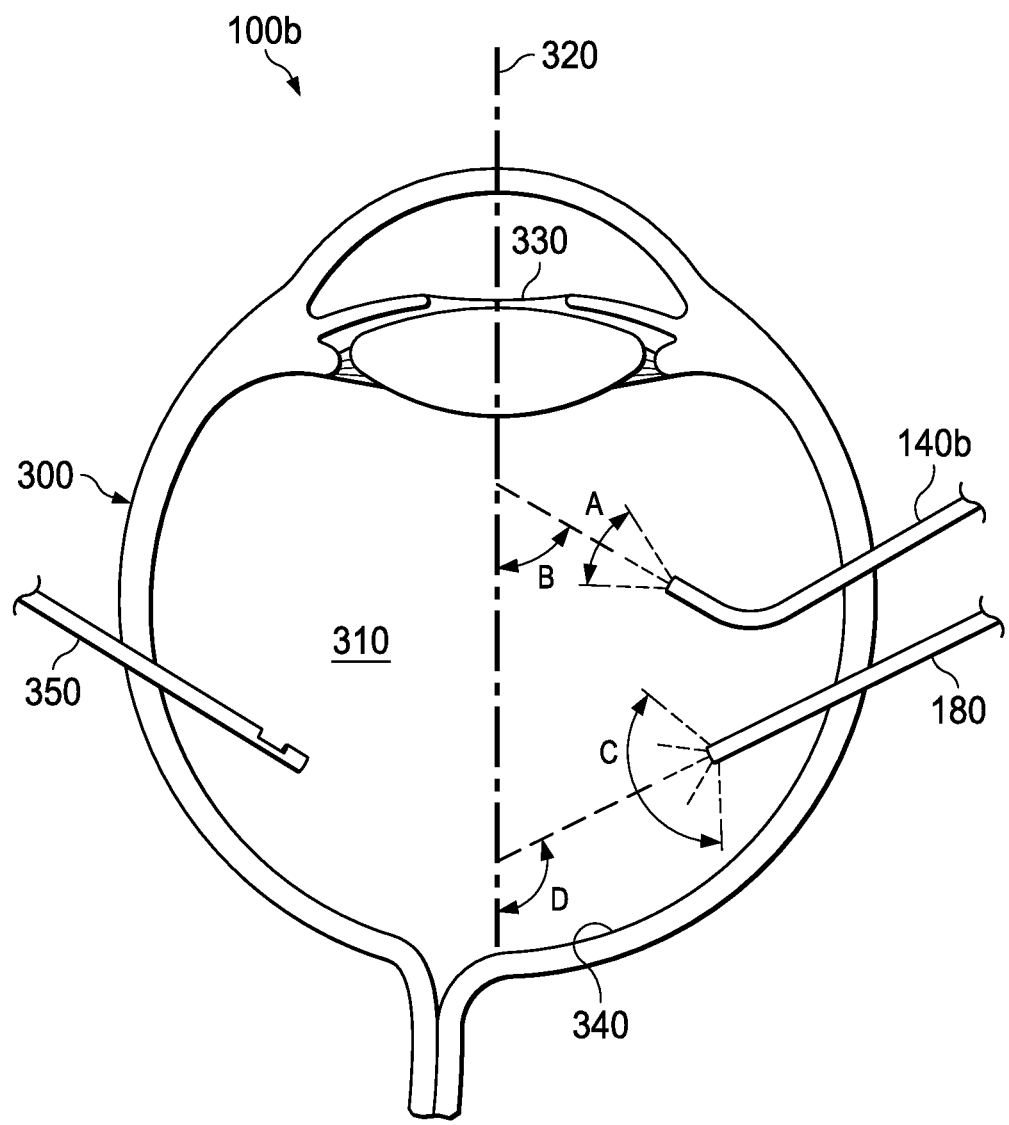
FIG. 3 is a schematic representation of surgical instruments of another vitreous visualization system, including a separate curved vitreous visualization tool and general illumination tool both inserted in an eye to allow visualization of the vitreous during ophthalmic surgery.
Figure 4:
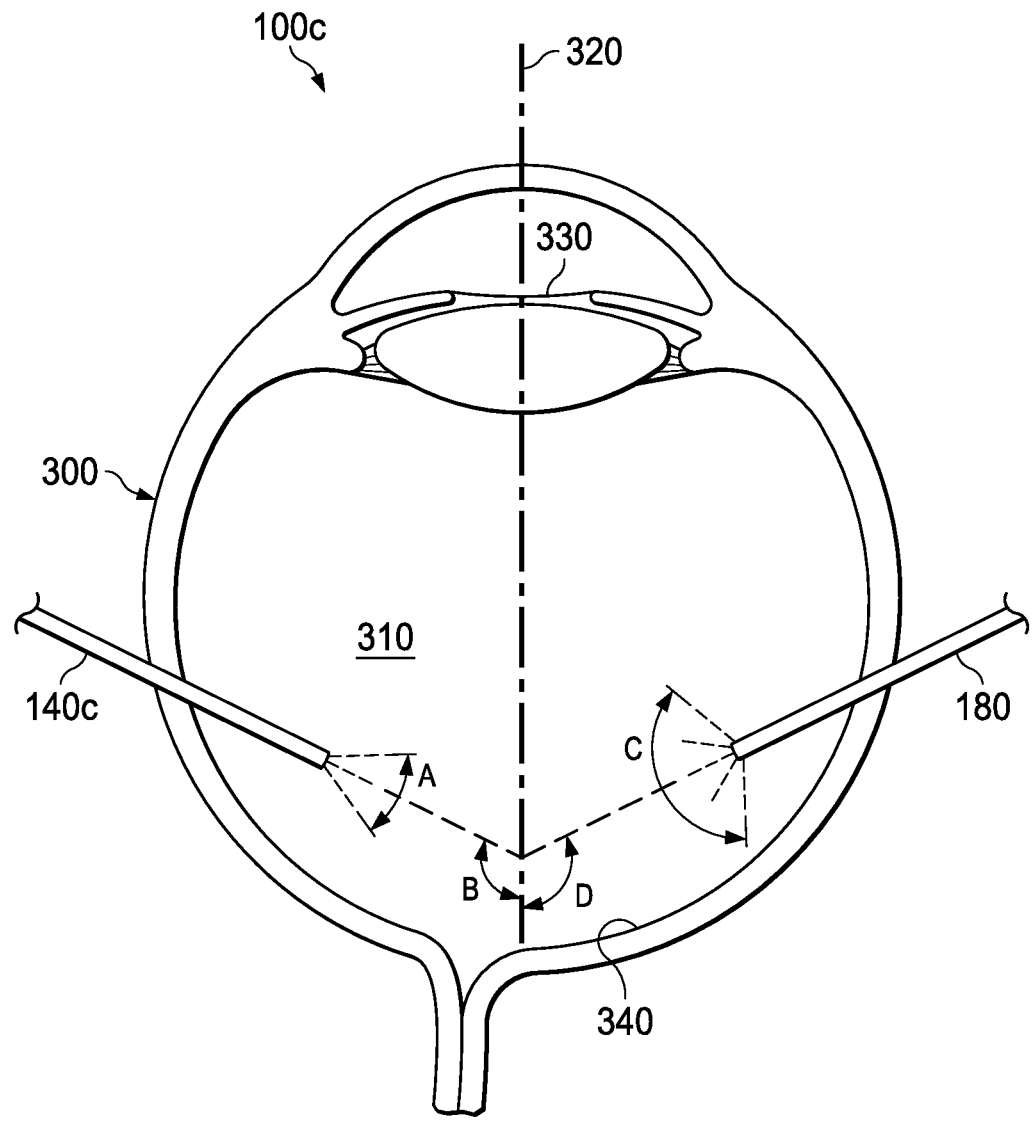
FIG. 4 is a schematic representation of a vitreous visualization system, including a combined vitreous visualization tool and surgical tool a general illumination tool inserted in an eye to allow visualization of the vitreous during ophthalmic surgery.

If present, as shown in FIGS. 2-4, general illuminator 150 may provide light from general illumination tool 180 with a broad angle of illumination, C, which may be at least 75 degrees, at least 80 degrees, at least 90 degrees, at least 120 degrees, at least 150 degrees, or at least 30 degrees greater than angle A. In addition, the angle between the center of angle of illumination C and the vitreous-pupil axis of eye 300, indicated as angle D, may be at least 90 degrees, at least 120 degrees, at least 150 degrees, at least 180 degrees, or at least 30 degrees greater than angle B. Angle D may vary widely depending on the surgical procedure. When access to peripheral areas of the eye is needed, the eye may be rotated significantly a general illumination tool 180 may be moved to a large angle D.

In addition to the factors discussed above, visibility of the vitreous may be improved by differences in the wavelengths of light provided by vitreous visualization light source 120 and general light source 160. For instance general light source 160 may provide white light, while vitreous visualization light source 120 may provide green light, such as described in further detail in FIGS. 7-10. In general, light having shorter wavelengths, such as green or blue, scatters better in the vitreous than light having longer wavelengths, such as red. Accordingly, shorter wavelength light may better facilitate vitreous visualization. In addition, red and orange light, due to their similarities to retina color, may not improve vitreous visualization as much as colors less similar to retina color. However, shorter wavelengths of light may be more likely to cause accidental damage to the eye, such as a, hakic hazard such that very short wavelengths may not be used, even if they provide more improvements in vitreous visualization. In general, light from vitreous visualization light source may have a wavelength in the range of 480-530 nm (aqua to green-yellow). Wavelengths in the range of 510-530 nm may be used to take advantage of readily available green diodes, such as green diodes that produce light in the 510-520 nm range.

Further, vitreous illuminator 110 may provide light in a flashing or pulsing pattern to further enhance visibility of the vitreous, particularly when general illuminator 150 provides white light. The flashing or pulsing pattern may be controlled by processor 190 or another processor and may be started or stopped or otherwise controlled by controller 200.

Referring now to FIG. 2, a portion of vitreous visualization system 100a is shown inserted in eye 300 during ophthalmic surgery. Both vitreous visualization tool 140a and general illumination tool 180 are inserted into vitreous 310 of eye 300. Eye 300 has a vitreous-pupil axis 320, that is determined with respect to pupil 330.

Vitreous visualization tool 140 provides light with a low angle of illumination, A, the center of which forms angle B with vitreous-pupil axis 320. General illumination tool 180 provides light with a broad angle of illumination, C, the center of which forms angle D with vitreous-pupil axis 320. Angles B and D are such that general illumination tool 180 tends to illuminate the retina 340, while vitreous visualization tool 140a tends to illuminate the vitreous 310.

One or more additional surgical tools, such as vitrectomy probe 350, may also be inserted into eye 300. Improved visualization of vitreous 310 may allow such additional surgical tools to be used more safely or efficiently.

In order to further increase angle B, vitreous visualization system 100b may include vitreous visualization tool 140b, which is curved as shown in FIG. 3 so that its tip may be oriented more in the direction of pupil 330 and less in the direction of retina 340 when it is inserted in eye 300. The angle and dimensions of the curve of vitreous visualization tool 140b may be determined by the optical properties of its component materials, such as an optical fiber, as well as the need to be able to insert it into eye 300 without undue damage. For instance, the curve may have a bend angle of between 35 and 45 degrees.

As shown in FIG. 4, vitreous visualization system 100c may include a combined vitreous visualization tool/surgical tool 140c. In the example shown, the surgical tool portion of combined vitreous visualization tool/surgical tool 140c is a vitrectomy probe, but combinations with other surgical tools, such as an infusion cannula, are also possible. Depending on the surgical tool, vitreous visualization tool/surgical tool 140c may remain largely in place or it may be moved frequently during the ophthalmic surgery. Due to the combination with a surgical tool, vitreous visualization tool/surgical tool 140c may reduce trauma to eye 300 by allowing one fewer incision in the eye. The same is true for other combined tools 140.

Figure 5:
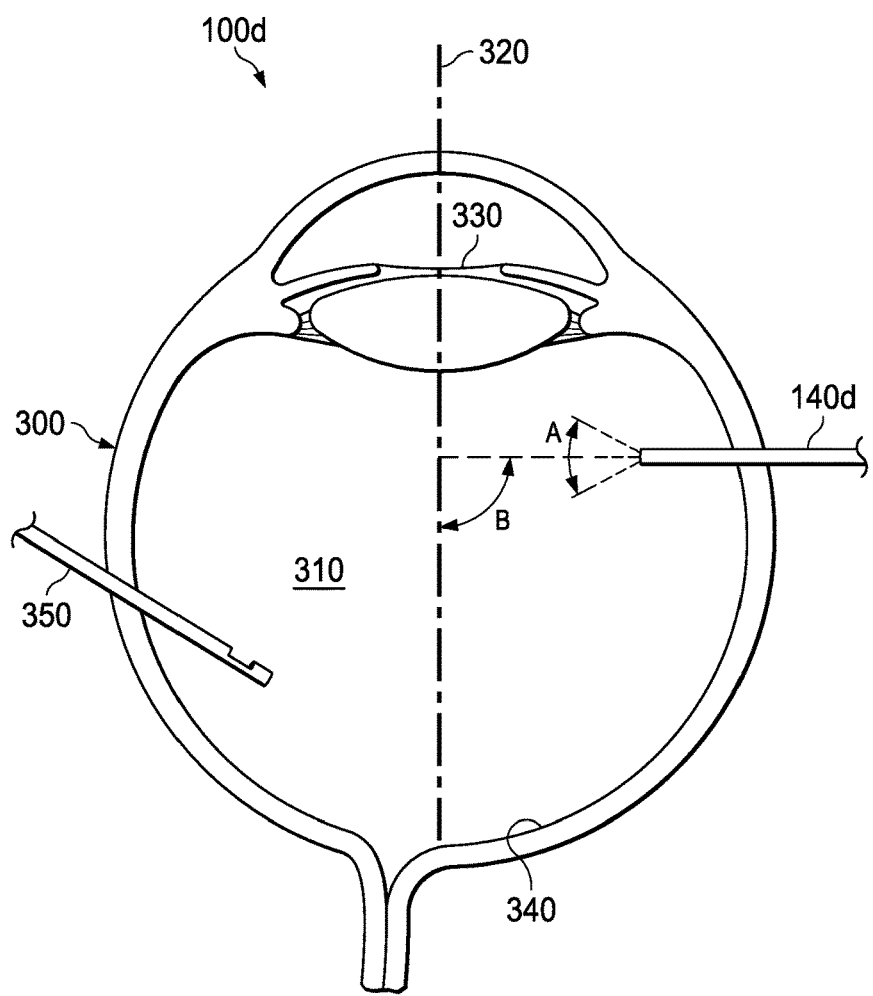
FIG. 5 is a schematic representation of a vitreous visualization system, including a vitreous visualization tool and no general illumination tool inserted in an eye to allow visualization of the vitreous during ophthalmic surgery.

As described above with respect to FIG. 1, some vitreous visualization systems, such as vitreous visualization system 100d of FIG. 5, may include only vitreous illuminator 110, such that only vitreous visualization tool 140d is inserted in eye 300, with no general illumination tool. This configuration may provide a very high ratio of brightness of the vitreous 310 to brightness of the retina 340. In addition, when separate vitreous visualization is no longer needed, for example after completion of a vitrectomy, vitreous visualization tool 140d may then instead be used as a general illumination tool. Adjustments to the light provided, its angle with the vitreous-retina axis, and other parameters may be performed at that time.

Although FIGS. 2-5 illustrate one vitreous illuminator 110 with one vitreous visualization tool 140 and one general illuminator 150 with one general illumination tool 180, if present, multiple instances of illuminators and tools maybe used. In addition, features of the various figures may be combined or duplicated without departing from the principles of this disclosure. For example, a combination vitreous visualization tool/surgical tool 140c such as that illustrated in FIG. 4 may be used as the sole vitreous visualization tool 140d in FIG. 5, or in combination with an additional straight or curved vitreous visualization tool 140a or 140b from FIGS. 2 and 3, respectively. Similarly, both straight and curved vitreous visualization tools 140a and 140b from FIGS. 2 and 3, respectively, may be used in combination. Although vitreous illuminator 110 is shown with one vitreous visualization tool 140 in FIG. 1, multiple vitreous visualization tools 140 may actually be combined with the same vitreous illuminator 110.

When more than one vitreous visualization tool 140 is present in eye 300, they may be used in different ways, such as at different angels B with the vitreous-pupil axis 320, with different angles of illumination A, or to provide different wavelengths of light or luminous flux.

Figure 6:
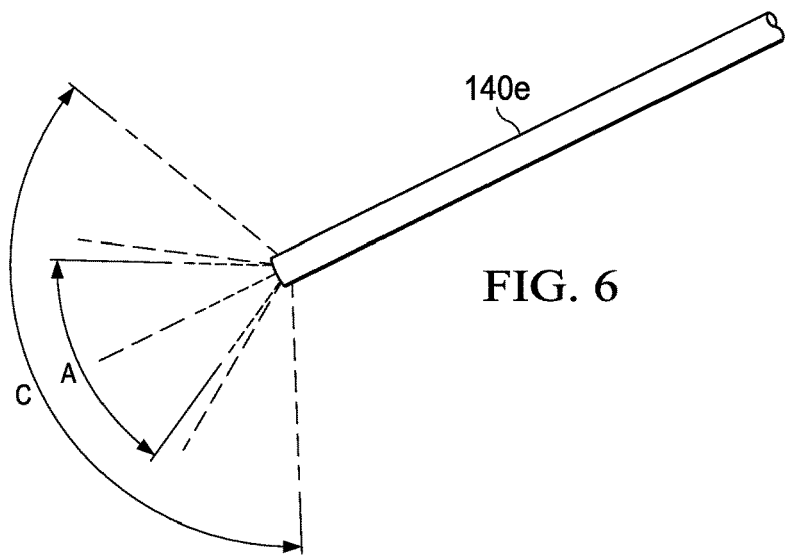
FIG. 6 is a schematic representation of light from a combined vitreous visualization tool and general illumination tool inserted in an eye to allow visualization of the vitreous during ophthalmic surgery.

Furthermore, vitreous visualization system 100 may have a single combined vitreous visualization and general illumination tool 140e, which may be inserted in eye 300 in a manner similar to combined vitreous visualization tool/surgical tool 140c of FIG. 4. As illustrated in FIG. 6, such a combined tool may provide a low angle of illumination A of more intense or different wavelengths of light for vitreous visualization and a broad angle of illumination C of less intense or white light for general illumination.

Such combined vitreous visualization and general illumination tools 140e may have a dual-fiber configuration, such as the use of two optical fibers in the same tool, or the use of a multi-core optical fiber. Light for vitreous visualization may be supplied to one optical fiber, such as the core optical fiber of a multi-core optical fiber, while light for general illumination may be supplied to another optical fiber such as an exterior optical fiber of a multi-core optical fiber.

For instance, combined vitreous visualization and general illumination tool 140e may include a core fiber that is single mode and has a diameter of between 15 μm and 25 μm, such as 20 μm. The core fiber may be surrounded by an exterior fiber with a diameter of between 100 μm and 500 μm, such as 400 μm. The numeric aperture of such a multi-core fiber may be determined by cladding surrounding it, an external medium, or both.

Another multi-core fiber might use a high-index core fiber, such a fiber with an index of up to 1.7, or between 1.40 and 1.55, such as between 1.45 and 1.52 in the visible light range with a slightly lower-index external fiber. The index difference between the fibers controls the numeric aperture of the fiber, with a smaller different resulting in lower numeric aperture. The high-index core fiber may have a small numeric aperture, such as less than 1 or less than 0.12 while the lower-index external fiber may have a higher numeric aperture, such as greater than 0.20 or greater than 0.25. Such an optical fiber may be used with a single light source. The ratio of light delivered to the core fiber versus the external fiber may be controlled by the ratio of numeric apertures, by the spot and spot size of where the light enters the core, or any combination thereof.

A combined vitreous visualization and general illumination tool 140e may also include a single optical fiber, such as a standard general illumination fiber, that transmits light for vitreous visualization and light for general illumination. For instance, a laser may provide light for vitreous visualization while a white light source may provide light for general illumination. A dichroic filter may combine the laser light with the white light to form a collimated beam, which may then pass through a condensor, so that both light from the laser and light from the white light source for general illumination are coaxial and focused into the optical fiber of the combined vitreous visualization and general illumination tool 140e.

In a specific vitreous visualization system 100e, depicted in FIG. 7, a combined vitreous visualization and general illumination tool 140f is provided. Tool 140f includes vitreous visualization light source 120. Tool 140f is also a component of general illuminator 150, which also includes general light source 160 and general conduit 170, that transmits light from general light source 160 to tool 140f. Optional components 190, 200, 210, and 220 of vitreous visualization system 100e may be as described with respect to FIG. 1.

As illustrated in FIG. 9, general conduit 170 may include cable 400, which includes a conduit portion of a general illumination optical fiber, with connector 410 at one end, which may be plugged into general light source 160 to allow transmission of light through general conduit 170. Connector 410 may be a fiber optic ACMI connector.

The other end of cable 400 attaches to combined vitreous visualization and general illumination tool 140f at conduit attachment 420 so that light transmitted through cable 400 may enter tool 140f. As described further with respect to FIG. 9, the general illumination optical fiber 500 in cable 400 may have a tool portion that passes through conduit attachment 420, tool housing 430, and probe tip 440, where it may enter the eye if probe tip 440 is inserted in the eye.

Light for vitreous visualization is generated within tool 140f and may also pass through probe tip 440 and into the eye, if probe tip 440 is inserted in the eye. Light for vitreous visualization may be turned on or off with control 450, which may be a simple on/off switch (not shown) or a combined on/off and luminous flux control switch, such as the switch depicted in which and up/down movement turns light for vitreous visualization on or off, while rolling the wheel controls luminous flux. Levers and pressure sensors may also be used in a combined or separate luminous flux control (not shown).

Control 450 may be electrically connected to laser 460 via circuit 470, such as the flexible circuit depicted. Laser 460 may include a diode laser or other laser. It may further include a circuit board and a microprocessor, as shown. Alternatively, laser 460 may be controlled by an external processor which may be connected to control 450 or another control.

Combined vitreous visualization and general illumination tool 140f may include an internal power source, such as a battery 480, which may provide a 6V direct current or a direct current less than 6V. The internal power source may provide energy to laser 460 as well as any component circuit board or microprocessor. Power may alternatively be provided by an external source.

Laser 460 may produce light having a particular wavelength, such as wavelengths in the green spectrum of visible light, or tool 140f may contain a dichoric filter so that only a particular wavelength of enters vitreous visualization optical fiber 480. Laser 460 may, in particular, be a Class 2 green diode laser that produces light with a wavelength in the range of 510-520 nm. In order to avoid phototoxicity or other negative effects, laser 460 may have a luminous flux of 6 mW or lower. Further, laser 460 may regulate its luminous flux using photodiodes and hardware loops. These features may be arranged such that laser 460 always turns on at its lowest luminous flux, further avoiding phototoxicity or other negative effects.

A light beam from laser 460 is transmitted to vitreous visualization optical fiber 480, which transmits the light through probe tip 440 so it may exit combined vitreous visualization and general illumination tool 140f After leaving laser 460 and prior to entering optical fiber 480, the light beam may pass through one or ore optical components, which may alter the light beam. As illustrated in FIG. 9, the light beam first passes through collimator 490, then through condenser 510 before entering optical fiber 480.

General illumination optical fiber 500 runs from conduit attachment 420, through housing 430, and joins vitreous visualization optical fiber 480 in probe tip 440. Probe tip 440 may include a thin tube, such as a metal tube, that surrounds general illumination optical fiber 500 and vitreous visualization optical fiber 480.

The relative size and numeric aperture of general illumination optical fiber 500 and vitreous visualization optical fiber 480 control their angles of illumination, A and C, which determine the light cone projected from the fibers. As shown in FIG. 9, when viewed at an axial distance of 10 mm, angle of illumination A may produce light cone 600, while angle of illumination C may produce light cone 610. Light cone 610 may have a diameter two to three times larger than that of light cone 600. In addition, light cone 610 may be white, while light cone 600 may be green or another color produced by laser 460 or resulting from a dichoric filter in tool 140f.

Combined vitreous visualization tool 140f and vitreous visualization system 100e and components thereof may be combined with other elements of vitreous visualization tools and systems described herein unless clearly mutually exclusive. For instance the laser and general illumination light sources in vitreous visualization system 100e may be used with other vitreous visualization systems described herein.

The present disclosure further includes a method of illuminating the vitreous of the eye, for instance during ophthalmic surgery such as vitreoretinal surgery and particularly during a vitrectomy. In the method, a vitreous illuminator such as described herein is used as described herein to illuminate to the vitreous of the eye to allow its visualization. In particular, the vitreous illuminator may provide light with an angle of illumination, at an angle with the vitreous-pupil axis, with a luminous flux, in a pulsed pattern, or at a wavelength that facilitates vitreous visualization. The vitreous, thus rendered visible, may then be removed using a vitrectomy probe. Alternatively, it may be avoided and not removed if desired during the surgery. Once the need to visualize the vitreous has passed, the vitreous illuminator may be switched off or used for another purpose or removed from the eye to protect against phototoxicity or to allow the insertion of other instruments.

The above disclosed subject matter is to be considered illustrative, and not restrictive, and the appended claims are intended to cover all such modifications, enhancements, and other embodiments which fall within the true spirit and scope of the present disclosure. For example, although vitreous visualization is most commonly needed during ophthalmic surgery, if it were useful in another procedure, such as a purely diagnostic procedure not otherwise considered to be surgery, the systems and methods described herein may be employed.

The invention claimed is:

1. A vitreous visualization system comprising:
    a vitreous illuminator comprising:
        a vitreous visualization light source; and
        a vitreous visualization tool that is configured to transmit light from the vitreous visualization light source into an eye having vitreous, a pupil, and a vitreous-pupil axis;
    a general illuminator comprising:
        a general light source; and
        a general illumination tool that is configured to transmit light from the general light source into the eye;
    wherein the vitreous visualization tool and the general illumination tool form a combined tool;
    wherein the combined tool comprises a multi-core optical fiber having a core optical fiber that transmits light from the vitreous visualization light source and an exterior optical fiber that transmits light from the general light source.

2. The vitreous visualization system of claim 1, further comprising a vitreous conduit that transmits light from the vitreous visualization light source to the vitreous visualization tool.

3. The vitreous visualization system of claim 1, wherein the vitreous visualization light source is located within the vitreous visualization tool.

4. The vitreous visualization system of claim 1, wherein the vitreous visualization light source generates light at a wavelength corresponding to a visible color and the general light source generates white light.

5. The vitreous visualization system of claim 1, wherein the vitreous visualization light tool is configured to transmit light into the eye at an angle of illumination A that is less than 45 degrees.

6. The vitreous visualization system of claim 1, wherein the vitreous visualization tool has a numeric aperture of less than 0.30.

7. The vitreous visualization system of claim 1, wherein the general illumination tool is configured to transmit light into the eye at an angle of illumination C, which is less than 75 degrees.

8. The vitreous visualization system of claim 1, wherein a luminous flux of the vitreous illuminator, as measured at a tip of the vitreous visualization tool, is at least five times higher than a luminous flux of the general illuminator, as measured at a tip of the general illumination tool.

9. The vitreous visualization system of claim 1, wherein the vitreous visualization tool is configured to transmit light into the eye at an angle of illumination A, and wherein an angle B formed between a center of angle of illumination A and the vitreous-pupil axis is less than 100 degrees.

10. The vitreous visualization system of claim 1, wherein the general illumination tool is configured to transmit light into the eye at an angle of illumination C, and wherein an angle D formed between a center of angle of illumination D and the vitreous-pupil axis is at least 90 degrees.

11. The vitreous visualization system of claim 10, wherein the vitreous visualization tool is configured to transmit light into the eye at an angle of illumination A, and wherein an angle B formed between a center of angle of illumination A and the vitreous-pupil axis is less than 100 degrees.

12. The vitreous visualization system of claim 1, wherein the vitreous illuminator generates pulses of light.

13. The vitreous visualization system of claim 1, wherein the vitreous visualization tool is configured to have a luminous flux at its tip within the eye of 10 lumens or less.

14. The vitreous visualization system of claim 1, wherein a distance between the vitreous visualization light source and the vitreous is configured to be less than three meters.

15. The vitreous visualization system of claim 1, wherein the vitreous visualization tool is combined with a surgical tool.

16. The vitreous visualization system of claim 1, wherein the vitreous visualization light source and the general light source are a single combined light source.

17. The vitreous visualization system of claim 1, wherein the vitreous visualization light source is a monochromatic laser and the general light source is a white light source.

18. The vitreous visualization system of claim 1, wherein the vitreous visualization light source is a monochromatic laser and the general light source is a supercontinuum laser.

19. A vitreous visualization system comprising a vitreous illuminator comprising:
   a vitreous visualization light source; and
   a vitreous visualization tool that is configured to transmit light from the vitreous visualization light source into an eye having vitreous, a pupil, a vitreous-pupil axis, and a retina at an angle B with the vitreous-pupil axis of the eye such that a brightness of the vitreous in the eye is higher than a brightness of the retina of the eye;
   a general illuminator comprising:
      a general light source; and
      a general illumination tool that is configured to transmit light from the general light source into the eye;
   wherein the vitreous visualization tool and the general illumination tool form a combined tool;
   wherein the combined tool comprises a single optical fiber that transmits both the light from the vitreous visualization light source and the light from the general light source;
   wherein the vitreous visualization light source is a monochromatic laser and the general light source is a white light source and wherein a dichroic filter combines the laser light from the vitreous visualization light source and the white light from the white light source to form a collimated beam to place on the single optical fiber of the combined tool.

20. The vitreous visualization system of claim 19, further comprising a vitreous conduit that transmits light from the vitreous visualization light source to the vitreous visualization tool.

21. The vitreous visualization system of claim 19, wherein the vitreous visualization light source is located within the vitreous visualization tool.

22. The vitreous visualization system of claim 19, wherein the vitreous visualization light tool transmits light into the eye at an angle of illumination A that is less than 45 degrees.

23. The vitreous visualization system of claim 19, wherein the vitreous visualization tool has a numeric aperture of less than 0.30.

* * * * *